US 6,690,959 B2

(12) United States Patent
Thompson (10) Patent No.: US 6,690,959 B2
(45) Date of Patent: Feb. 10, 2004

(54) SKIN-MOUNTED ELECTRODES WITH NANO SPIKES

(75) Inventor: David L. Thompson, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 154 days.

(21) Appl. No.: 09/944,821

(22) Filed: Aug. 31, 2001

(65) Prior Publication Data

US 2002/0028991 A1 Mar. 7, 2002

Related U.S. Application Data

(60) Provisional application No. 60/229,925, filed on Sep. 1, 2000.

(51) Int. Cl.⁷ .................................................. A61B 5/04
(52) U.S. Cl. ......................... 600/372; 600/386; 600/393
(58) Field of Search ............................... 600/372, 382, 600/386, 393; 607/115, 142, 152

(56) References Cited

U.S. PATENT DOCUMENTS

| | | | |
|---|---|---|---|
| 3,814,097 A | 6/1974 | Ganderton et al. | 128/268 |
| 3,964,482 A | 6/1976 | Gerstel et al. | 128/260 |
| 4,004,578 A | * 1/1977 | Palmius | 600/392 |
| 4,311,152 A | 1/1982 | Modes et al. | 128/641 |
| 4,556,063 A | 12/1985 | Thompson et al. | 128/419 PT |
| 4,685,466 A | * 8/1987 | Rau | 600/387 |
| 4,821,723 A | 4/1989 | Baker, Jr. et al. | 128/419 D |
| 4,837,049 A | * 6/1989 | Byers et al. | 427/96 |
| 4,920,968 A | * 5/1990 | Takase | 600/393 |
| 4,927,408 A | * 5/1990 | Haak et al. | 604/20 |
| 4,987,897 A | 1/1991 | Funke | 128/419 PG |
| 5,113,859 A | 5/1992 | Funke | 128/419 PG |
| 5,131,388 A | 7/1992 | Pless et al. | 128/419 D |
| 5,197,471 A | 3/1993 | Otero | 128/640 |
| 5,199,428 A | 4/1993 | Obel et al. | 128/419 C |
| 5,207,218 A | 5/1993 | Carpentier et al. | 128/419 PG |
| 5,250,023 A | 10/1993 | Lee et al. | 604/20 |
| 5,279,544 A | 1/1994 | Gross et al. | 604/20 |

(List continued on next page.)

FOREIGN PATENT DOCUMENTS

| | | | |
|---|---|---|---|
| EP | 0 571 120 A1 | 11/1993 | A61B/5/0408 |
| WO | WO 96/37256 | 11/1996 | A61N/1/30 |
| WO | WO 97/48422 | 12/1997 | A61N/1/30 |
| WO | WO 97/48440 | 12/1997 | A16N/1/30 |
| WO | WO 97/48441 | 12/1997 | A61N/1/30 |
| WO | WO 98/25517 | 6/1998 | A61B/5/0408 |
| WO | WO 99/00155 | 1/1999 | A61M/5/32 |

OTHER PUBLICATIONS

USSN 09/797,031, filed Mar. 1, 2001, based on USSN 60/186,235, filed Mar. 1, 2000, entitled "Implantable Medical Device With Multi–Vector Sensing Electrodes".

Primary Examiner—Carl Layno
(74) Attorney, Agent, or Firm—Girma Wolde-Michael; Elisabeth L. Belden (57) ABSTRACT

Epidermally mountable device includes terminus structures to enable positive connection with conductive tissue. The device includes nano spikes shaped to penetrate the epidermis of the skin to collect electrical biopotentials such as cardiac depolarization waveforms (ECGs) and various signals transmitted by implanted devices. Generally, the nano spikes are integrated on a substrate comprising, preferably, a flexible metalized conductive plate attachable to an adhesive backing. The device could be mounted on any external body of the patient to collect ECG, EEG or other signals. Further, the device is adaptable to include a programmable microprocessor, including memory and an antenna to store, receive and transmit data as needed. In one embodiment, in addition to collecting physiologic data through direct contact, the device may also be used as a smart patch to download, store and transfer data from implanted medical devices or other data sources using wireless data transmission medium.

18 Claims, 7 Drawing Sheets

U.S. PATENT DOCUMENTS

| | | | |
|---|---|---|---|
| 5,309,909 A | 5/1994 | Gadsby et al. | 128/639 |
| 5,311,396 A | 5/1994 | Steffen | 361/736 |
| 5,312,446 A | 5/1994 | Holschbach et al. | 607/9 |
| 5,314,430 A | 5/1994 | Bardy | 607/5 |
| 5,330,507 A | 7/1994 | Schwartz | 607/14 |
| 5,331,966 A | 7/1994 | Bennett et al. | 128/696 |
| 5,345,362 A | 9/1994 | Winkler | 361/381 |
| 5,354,316 A | 10/1994 | Keimel | 607/15 |
| 5,458,141 A | 10/1995 | Neil | 128/641 |
| 5,480,842 A | 1/1996 | Clifton et al. | 437/226 |
| 5,545,186 A | 8/1996 | Olson et al. | 607/14 |
| 5,591,139 A | 1/1997 | Lin et al. | 604/264 |
| 5,683,432 A | 11/1997 | Goedeke et al. | 607/32 |
| 5,701,895 A | 12/1997 | Prutchi et al. | 128/630 |
| 5,843,139 A | 12/1998 | Goedeke et al. | 607/32 |
| 5,855,801 A | 1/1999 | Lin et al. | 216/2 |
| 6,050,988 A | 4/2000 | Zuck | 604/890.1 |
| 6,115,636 A | 9/2000 | Ryan | 607/60 |
| 6,117,077 A * | 9/2000 | Del Mar et al. | 600/301 |
| 6,161,039 A | 12/2000 | Krichen et al. | 600/523 |
| 6,171,239 B1 * | 1/2001 | Humphrey | 600/372 |
| 6,200,265 B1 | 3/2001 | Walsh et al. | 600/300 |
| 6,201,982 B1 | 3/2001 | Menkes et al. | 600/386 |
| 6,510,333 B1 * | 1/2003 | Licata et al. | 600/383 |

\* cited by examiner

SKIN-MOUNTED ELECTRODES WITH NANO SPIKES

This application claims the benefit of Ser. No. 60/229,925 filed on Sep. 1, 2000.

FIELD OF THE INVENTION

The present invention generally relates to medical devices. Specifically the invention relates to skin mounted electrodes with substantially short nano spikes that are easily attachable to human skin. More specifically, the invention relates to electrodes that provide substantially positive and reliable contact without the need for using gels, shaving and/or sanding of the skin surface to enable positive electrical electrode attachment.

BACKGROUND OF THE INVENTION

Epidermal attachments for physiological data collection such as ECG and EEG sensing and transdermal delivery of peptides, proteins, various agents and drugs to the human body are some of the medically useful applications for skin mounted medical devices. Some of these devices require mechanical disruption of the skin in order to enhance transdermal flux such as disclosed in U.S. Pat. No. 3,814,097 issued to Ganderton et al, U.S. Pat. No. 5,279,544 issued to Gross et al, U.S. Pat. No. 5,250,023 issued to Lee et al., and U.S. Pat. No. 3,964,482 issued to Gerstell et al. These devices typically utilize tubular or cylindrical structures generally, although the Gerstell invention uses an array of solid or hollow microneedles to penetrate through the stratum corneum into the epidermal layer, but not to the dermal layer. PCT applications WO 97/48440, WO 97/48441, and WO 97/48442 by Cormier et al employ a plurality of solid metallic microblades and anchor elements, etched from a metal sheet, with a length of 25–400 mm. PCT application WO 96/37256, by Godshall discloses another microblade structure with blade lengths of 10–20 mm for enhancing transdermal delivery.

Another example of a needle that penetrates into the dermis is provided in U.S. Pat. No. 5,591,139, WO 99/00155, and U.S. Pat. No. 5,855,801 all issued to Lin. These patents and publications disclose how the needles are processed using integrated circuit fabrication techniques. The needles used have a length in the range of 1,000 to 6,000 microns.

U.S. Pat. No. 5,309,909 issued to Gadsby et al., discloses a combined skin preparation and monitoring electrode. The electrode is designed to reduce motion artifacts in recording biopotentials by penetrating a patient's skin prior to acquiring biopotentials. Penetration of the skin reduces the skin impedance and the skin's propensity to generate motion artifacts. The electrode includes a resilient dome with penetration tines extending from the concave inner surface of the dome. Upon application of a force, the dome moves from a first position to second position forcing the penetration tines into a patient's skin. Upon removal of the force, the dome moves back to its original configuration withdrawing the penetration tines from the patient's skin.

U.S. Pat. No. 5,197,471 issued to Otero, discloses a dry electrode for medical use to record existent biopotentials on the skin surface and for electrical stimulation of different zones of the human body. The dry electrode comprises a flexible electro-conductive plate provided on its bottom side with a plurality of sharp bosses for partial skin penetration. The plate includes a corrugated radial extension tongue and two orifices, the first orifice in the center of the plate and a second orifice in the tongue portion. The orifices in the tongue portion allow for different connectors to be utilized, such as a stem with a circular base, a Stillson wrench or a hook type connection. The electrode makes contact on its bottom face with a needle that penetrates and stays anchored within the skin.

U.S. Pat. No. 4,311,152, issued to Modes et al., discloses a medical electrode and skin preparation device adapted to be secured to the skin and designed to prepare the skin by penetration of the epidermal layer of the skin in contact with the electrical conductor of the electrode after the electrode is secured in place on the skin. The electrode includes an abrading member associated with an electrical conductor capable of transmitting biopotential events for recording, with the electrical conductor retained by a collar and an adhesive-coated pad securing the electrode to the skin of the patient. The abrading member in contact with the skin is movable relative to the skin of the patient and collar by an applicator gun so as to allow penetration of the epidermal layer of the skin after the electrode is placed on the skin. Uniform skin preparation achieved by the electrode and applicator gun minimizes motion artifacts arising from skin potential variations.

U.S. Pat. No. 5,701,895, issued to Prutchi et al, discloses an implantable subcutaneous data port for transferring data received from a sensor implanted within a subject. The data port electrically connects to the sensor and includes a control circuit electrically connected to an access port. The control circuit includes a current loop transmitter that modulates a current loop signal with voltage outputs from the sensor. Needle electrodes (large minimum diameter) are insertable through the skin of the subject to the access port and provide an electrical interface between the control circuit and current loop receiver.

U.S. Pat. No. 6,050,988, issued to Zuck, discloses a device including a sheet member having a plurality of microprotrusions extending from a bottom edge for penetrating the skin of a patient. The sheet member, when in use, is oriented in an approximately perpendicular relation to the patient's skin. The microprotrusions penetrate the body surface to create good agent conduction from the system into the body or vice versa. Also, the microprotrusions or microblades are generally formed from a single piece of material and are sufficiently sharp and long for penetrating at least the stratum corneum of the skin.

U.S. Pat. No. 5,458,141, issued to Neil, discloses a medical electrode and a skin preparation device adapted to be secured to the skin of a patient and designed to prepare the skin by abrasion or penetration of the epidermal layer of the skin in contact with the conductive means of the electrode after the electrode is secured in place on the skin. The electrode includes a penetrating device associated with a conductor capable of transmitting biopotential events for recording, with the conductor being retained by an adhesive member that secures the electrode to the skin of the patient. The penetration device in contact with the skin is movable relative to the skin of the patient and a holder by an applicator gun to abrade or penetrate the epidermal layer of skin after the electrode is placed on the skin. Uniform skin preparation is achieved by a flexible screen member and electrolyte gel reservoir on the electrode and an applicator gun that minimizes motion artifacts arising from skin potential variations.

PCT publication WO 98/25517, by Svedman, discloses a device for sensing bioelectrical signals. Specifically, the invention relates to an electrode device that utilizes negative pressure and preferably heat to a portion of the epidermis causing interstitial fluid and/or the epidermal basement membrane to contact an electrode for a measuring operation.

Attachment devices exist for fixing EEG electrodes to a patient's scalp. These devices may use colloidal glue, adhesive tape or bandages. EEG electrodes may also be attached by incorporating them into web matrix helmets. Placing and removing these EEG electrodes from a patient's scalp is time consuming. The EEG electrodes are uncomfortable to wear and may lose signal contact during extended ambulatory monitoring. A quick-placement EEG electrode is described in U.S. Pat. No. 6,201,982 issued to Menkes and referenced herein in its totality. This patent proposes the continued use of gel as well as several connecting devices to replace current electrodes to ensure positive electrode contact.

Further, there is a need for a smart patch as described in U.S. Pat. No. 6,200,265 issued to Walsh and Thompson, which is incorporated herein by reference in its entirety. The patch electrode in the '265 patent describes the reception of uplink telemetry but it also requires, for at least one of its embodiments, the sensing of the ECG signal. The patch is easily attachable to a human skin to enable communication with medical devices and body bus systems as described in U.S. Pat. Nos. 4,987,897 and 5,113,859 issued to Funke, which are incorporated herein by reference in their entirety. Similarly, a smart patch can also enable communication with medical devices and body wave systems as described in U.S. Pat. No. 6,115,636 issued to Ryan, which is incorporated herein by reference in its entirety. In addition, a smart patch may be used to detect ECG signals for use in association with electrogram signals for identifying whether a lead is properly positioned during the operative implant procedure, as described in U.S. Pat. No. 6,161,039 issued to Krichen et al., which is incorporated herein by reference in its totality. Similarly and as would be easily evident to those skilled in the art, a smart patch might also be used to acquire ECGs for use in pacemaker and defibrillator follow-up sessions, troubleshooting post-implant, and transtelephonic monitoring, among others.

In PCT applications WO 97/48440, WO 97/48441, and WO 97/48442, to Cormier, the delivery of large molecule drugs through the skin is disclosed. Specifically, the disclosures relate to a non-conducting inert set of microblades to puncture the dead tissue that resides on human skin to a depth of ~10–20 microns.

SUMMARY OF THE INVENTION

The present invention implements specialized microblades or microneedles to provide a conductive system for use in electrical sensing applications to replace other apparatus, such as ECG electrodes, bioelectrical patches, among others. This invention may be used in replacement of various biosensing applications needing preparation of the skin such as shaving, sanding, gelling and similar procedures to enhance physiological signal sensing.

The present invention utilizes the layer of dead skin, the stratum corneum, that is normally not more than 10–20 microns in depth and makes up the outer layer of the human skin. The invention utilizes metalized nano spikes disposed on metalized electrode(s) to penetrate through the stratum corneum into the epidermal layer and enable data transmission from the epidermal layer to electrodes configured for connection to other medical devices.

In one embodiment, the nano spikes may provide a fixed, longer-term site so that the electrode may serve as an ECG sensing electrode. The invention provides a metalized contact area equipped with metalized nano spikes to make low impedance contact, thereby allowing good electrical contact for proper ECG sensing and/or electrical drive. The metalization may be applied, after completion of standard MEMs-like knife/needle/spike construction, by vapor deposition, electrolysis, or similar metallic deposition methods. The knives/needles have a substantially thin coating of conductive metal (10–100 angstroms) and connect to a backing plate that is preferably a metalized electrode. The advantages of having these spikes (~10 microns) are that they will not contact the nerves or the capillaries that are 200 to 300 microns deep. Thus, there is little or no pain/discomfort and no bleeding. Fitting over the metalized electrode is preferably an adhesive that is commonly available through a variety of manufacturers, such as 3M. The adhesives may be useful for short term use, for example, about two days, or long term, up to a week.

In yet another embodiment, the present invention may be adapted to serve as an electroencephalogram (EEG) electrode for making contact with a patient's head where a multiplicity of such electrodes are used. In this embodiment, a round preferably flexible substrate for each electrode is used to attach the nano spikes. These round electrodes are held in contact with the patient's head via a "netlike" structure, skull cap, helmet or similar configuration that provides pressure on the electrodes to maintain and ensure continuous contact of the electrodes with the scalp. The nano spike electrode of the present invention would advantageously replace the complex structure disclosed in the '982 patent.

In another embodiment, the present invention is implemented as a "smart patch" or extended memory device to receive Body Wave and Body Bus transmissions. Specifically, the invention relates to an electrode that is compatible with extended memory devices and other peripheral devices, mounted externally to patients, to provide communication with implantable devices in the patient. As a memory patch, the device's electrode would preferably be provided with a memory chip and a power source.

The present invention provides novel features in the implementation and use of extended memory patch as compared to disclosures in the '265 patent, as well as body wave and body bus system disclosed in the '636, '897, and '859 patents, respectively. The peripheral memory patch described in the '265 patent enables the extension of an implantable device's memory.

The present invention may be implemented to extend the memory capacity of implanted devices. Specifically, a memory patch may be taped either over the device (system A or B telemetry) or anywhere on the body (Body wave/bus technology in telemetry C). As the memory of the implanted device fills up, the device transmits the data to the external memory patch for storage, automatically. Such an operation allows one to perform a 24/48-hour Holter monitoring inexpensively in conjunction with or directly from implanted devices. This memory patch would only need to operate for, at most, a couple of days. These patches can be equipped with a much larger memory than what is normally found in an implantable device, thereby allowing for the storage of a greater amount of data. The procedure and process are inexpensive when particularly implemented as a tape-on, use-it-once device. Subsequently the data is downloaded and the patch thrown away. In this embodiment, the present invention uses a flexible "foil" battery commonly found in credit cards. The patch can be used at home and be equipped with an LED that would light up when the memory is filled up. Subsequently, the patient would remove the patch and mail it in to the doctor or a lab for analysis.

In yet another embodiment, the present invention can be adapted to accept more than one ECG electrode to monitor cardiac events, which, in the prior art, required a minimally invasive implantable device, such as described in U.S. Pat No. 5,987,352, issued to Klein, et al. and incorporated herein by reference in its entirety. The nano spikes of the present invention are electrically connected to a metalized electrode substrate and, through, it, to the ECG electrodes. When taped on, the circuitry could be tuned to pick the best vector (largest signal). This embodiment would use electronics similar to the type described in the '352 patent. Such electronics would be adapted to the present invention by miniaturization, and could be integrated with the metalized electrode substrate for secure placement on the patient's body.

BRIEF DESCRIPTION OF THE DRAIWNGS

DETAILED DESCRIPTION OF THE DRAWINGS

Generally, the present invention integrates microneedle/microblade technology with electroplating processes and methods to enable reliable sensing of bioelectrical signals such as ECGs, EEGs and the like.

Figure 1:
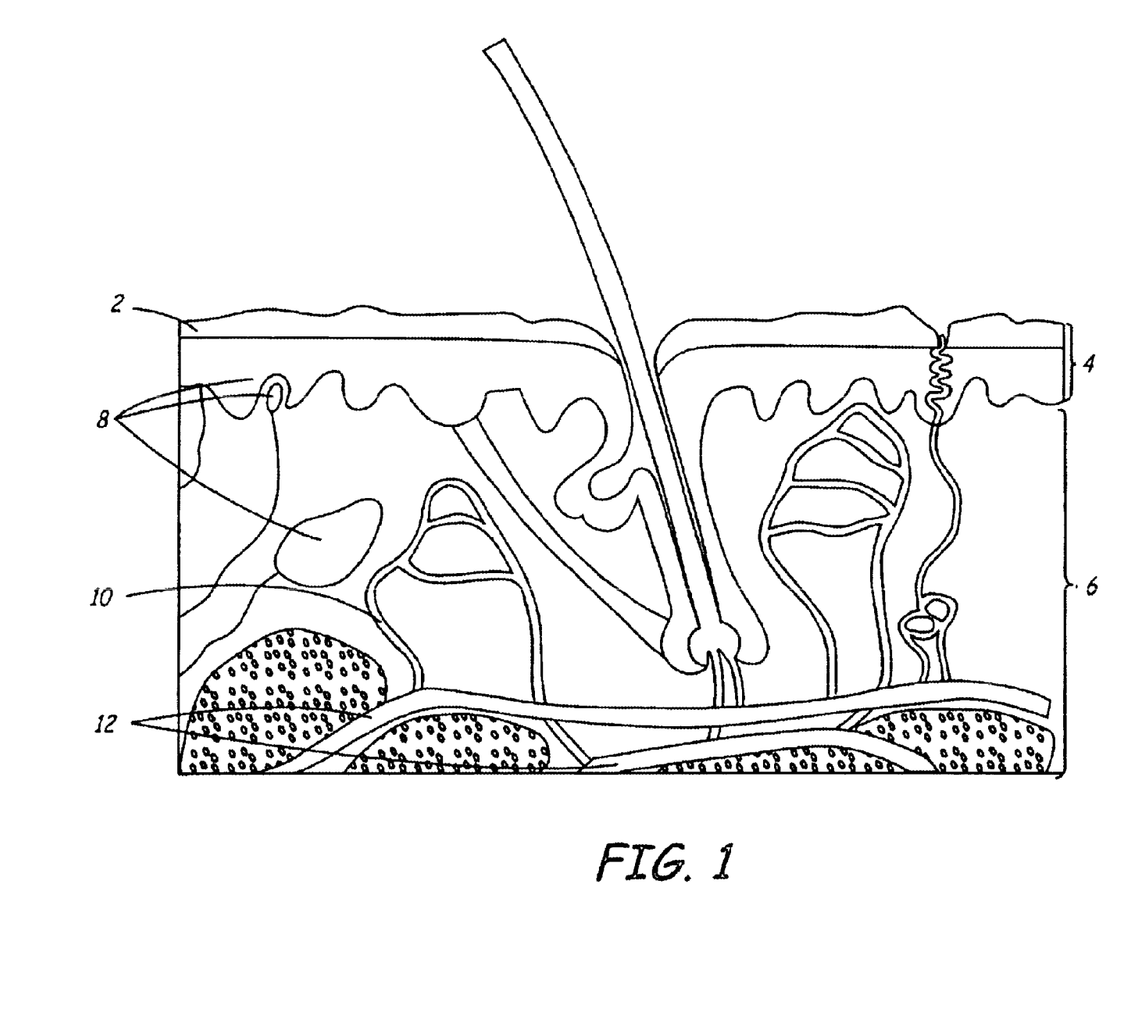
FIG. 1 is a cross section of the first two upper skin layers.

FIG. 1 depicts a cross section of human skin with various structures found therein. The human skin has a surface cornified layer (stratum corneum) 2 that is composed of dry, dead skin cells. Cornified layer, found in all humans, is approximately 10 to 20 microns in thickness and constitutes the uppermost layer of epidermis 2. Dermis 6 contains nerve endings 8 and capillaries 10, both of which rise Up meet the bottommost portions of epidermis 4. Veins and arteries 12 lie deeper in dermis 6 than other structures.

The nano spikes used in the present invention are approximately 10 microns in length. As such, they are long enough to penetrate through cornified layer 2 and reach epidermis 4. Once the nano spikes have penetrated epidermis 4, there is good contact with conductive tissue, tissue that carries electrical biopotentials such as cardiac depolarization waveforms (ECGs) as well as other electrical signals, such as those transmitted by implanted devices. The nano spikes are too short to penetrate dermis 6 and, therefore, will not under normal circumstances touch nerve endings 8 or penetrate capillaries 10 located in dermis 6. Thus, there is little chance for pain or bleeding with the use of the present invention.

Figures 2A, 2B:
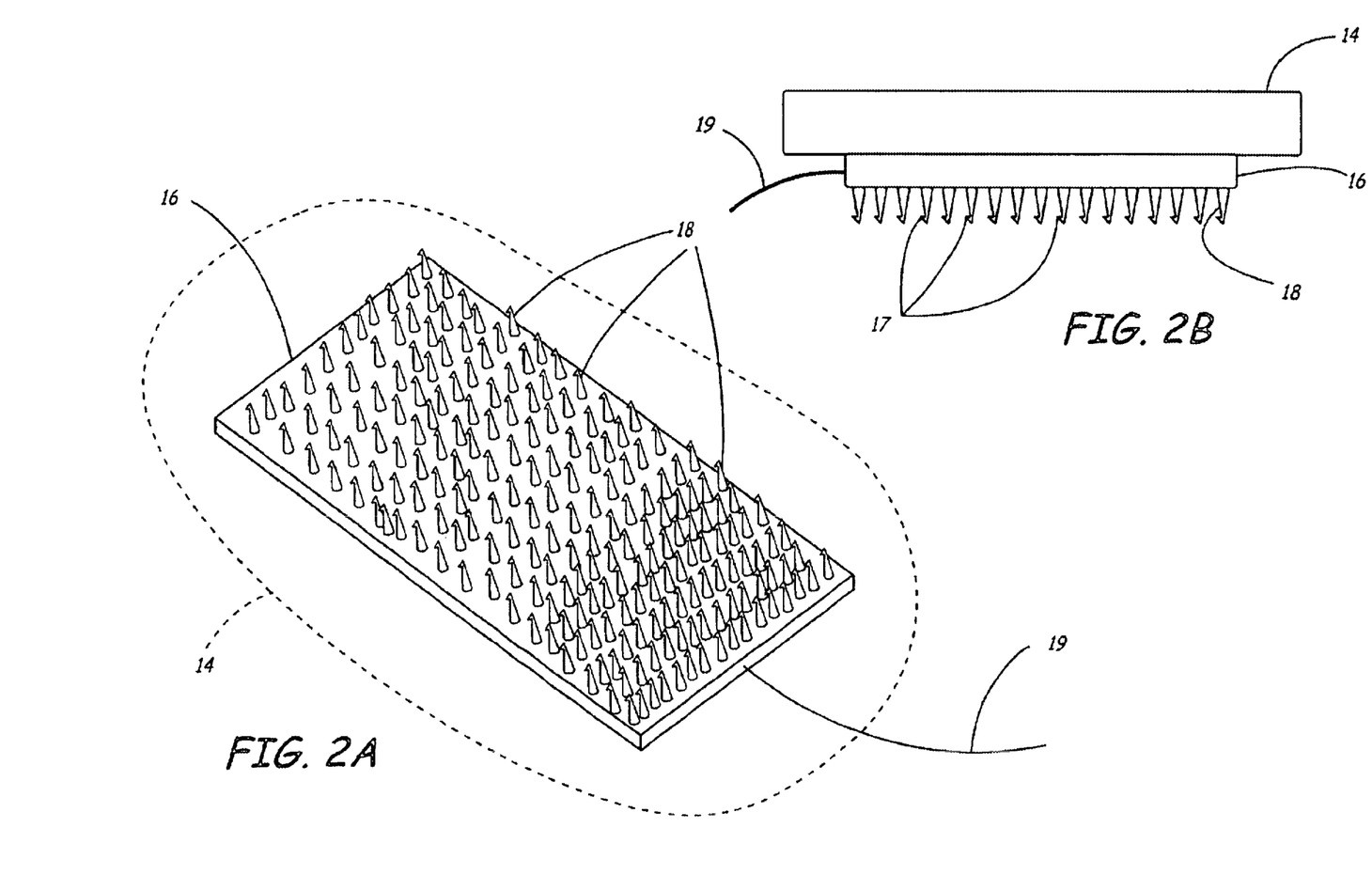
FIG. 2A is a perspective drawing of the skin-mounted electrode as used in the first embodiment. It illustrates the nano spikes embedded into the plate electrode that, in turn, is attached to an adhesive backing.
FIG. 2B is a cross section of skin-mounted electrode illustrating the layered effect of the adhesive, the electrode, and nano spikes, as used in the first embodiment.

FIG. 2a illustrates a skin-mounted electrode for use as an ECG electrode. FIG. 2a depicts the inverted skin-mounted electrode with metalized, conductive plate electrode 16 attached to adhesive backing 14. Plate electrode 16 includes a plurality of nano spikes 18, typically~10 microns in length, each of which is constructed for attachment to substrate plate electrode 16 forming angular protrusions thereof. Nano spikes 18 are sized and shaped to penetrate the stratum corneum 2 (FIG. 1) of the epidermis 4 (FIG. 1). Connective wire 19 typically terminates in a connection to an external pacemaker/defibrillator programmer, refer to FIG. 3.

The distribution and number of nano spikes 18 on electrode 16 may vary depending on the intended use. Typically, plate electrode 16 will be covered with hundreds of nano spikes 18 when used as a simple signal sensor.

Accordingly, the present invention provides a secure and reliable system for ECG sensing that is compatible with an external pacemaker/defibrillator programmer. In this embodiment, the skin-mounted electrodes are used in place of the usual ECG electrodes commonly found in the pacemaker/defibrillator follow-up clinic for use with an external programmer. The skin-mounted electrodes of the present invention are conveniently placed on the patient's skin by means of an adhesive that is larger than the metalized, conductive plate to which the nano spikes are attached. The "overlap" of the adhesive ensures continuous contact of the assembly to the patient's skin at desired locations on the patient's body to attain good ECG vectors for clinical diagnostic purposes.

FIG. 2b is a cross section of the skin-mounted electrode of the present invention. Adhesive backing 14 is used to ensure positional stability after placement of attached plate electrode 16. Nano spikes 18 protrude below plate electrode 16 and penetrate the stratum corneum 2, refer to FIG. 1. Angularly disposed end shapes, such as knives 17 illustrated in FIG. 2b according to one embodiment, protrude from ends of spikes 18 in order to ensure stable epidermal penetration of spikes 18 in the presence of body motion, underlying muscle movement and irregular skin or body topography. Conductive wire 19 provides connection to an external pacemaker/defibrillator/programmer or a similar device as depicted in FIG. 3.

Figure 3:
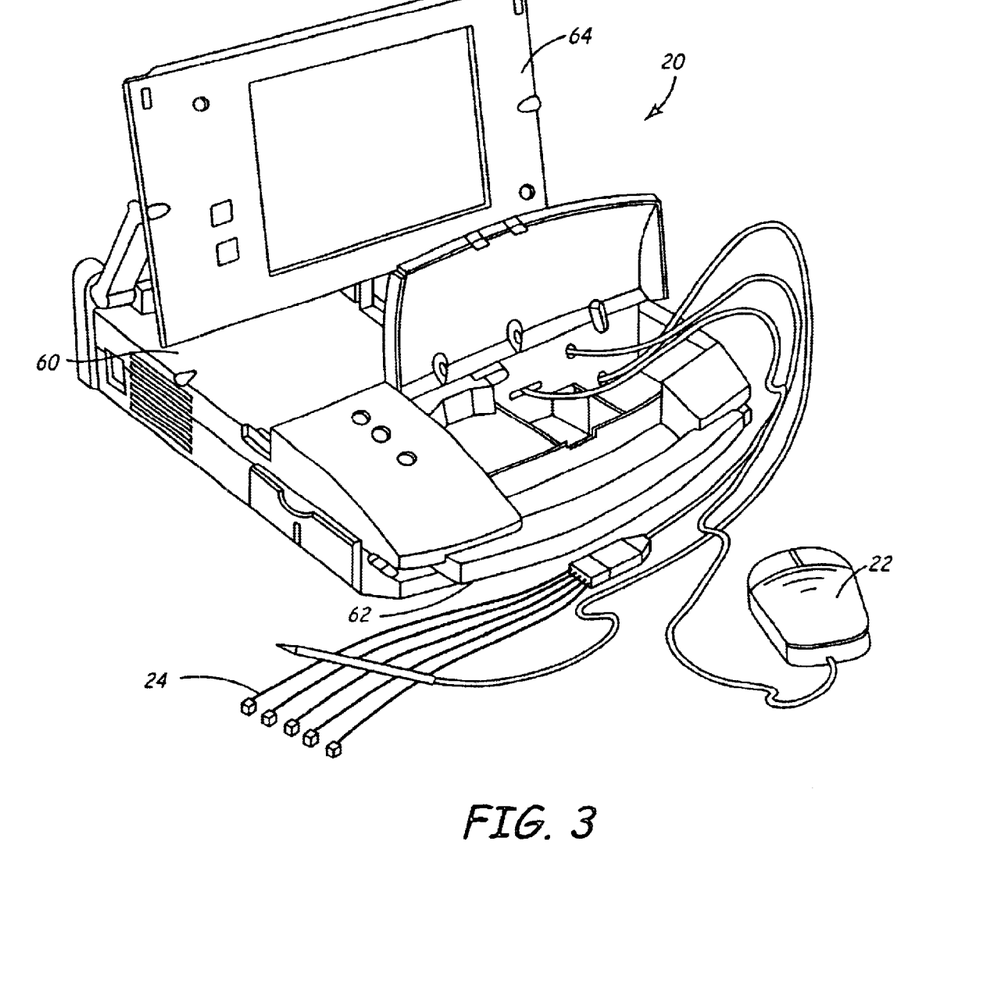
FIG. 3 is a perspective view of a programmer that may be used with the present invention to record real-time ECGs and to interrogate and download collected data.

FIG. 3 is a perspective view of programmer 20 that may be used in conjunction with the present invention to record real-time ECGs and to interrogate and download collected data. Internally, programmer 20 includes a processing unit (not shown) that in accordance with the present invention is a personal computer type motherboard, e.g., a computer motherboard including an Intel Pentium 3 microprocessor and related circuitry such as digital memory. The design details and operation of the programmer's computer system will not be set forth in detail in the present disclosure, as it is believed that such details are well-known to those of ordinary skill in the art.

Referring to FIG. 3, programmer 20 comprises an outer housing 60, which is preferably made of thermal plastic or another suitably rugged yet relatively lightweight material. A carrying handle, designated generally as 62 in FIG. 3, is integrally formed into the front of housing 60. With handle 62, programmer 20 can be carried like a briefcase.

An articulating display screen 64 is disposed on the upper surface of housing 60. Display screen 64 folds down into a closed position (not shown) when programmer 20 is not in use, thereby reducing the size of programmer 20 and protecting the display surface of display 64 during transportation and storage thereof.

A floppy disk drive is disposed within housing 60 and is accessible via a disk insertion slot (not shown). A hard disk drive is also disposed within housing 60, and it is contemplated that a hard disk drive activity indicator, (e.g., an LED, not shown) could be provided to give a visible indication of hard disk activation.

As would be appreciated by those of ordinary skill in the art, it is often desirable to provide a means for determining the status of the patient's conduction system. Normally, programmer 20 is equipped with external ECG leads 24 to which skin-mounted electrodes of the presently disclosed invention are operatively attached via connective electrical wire 19 (FIGS. 2a and 2b).

In accordance with the present invention, programmer 20 is equipped with an internal printer (not shown) so that a hard copy of a patient's ECG or of graphics displayed on the programmer's display screen 64 can be generated. Several types of printers, such as the AR-100 printer available from General Scanning Co., are known and commercially available.

In the perspective view of FIG. 3, programmer 20 is shown with articulating display screen 64 having been lifted up into one of a plurality of possible open positions such that the display area thereof is visible to a user situated in front of programmer 20. Articulating display screen is preferably of the LCD or electro-luminescent type, characterized by being relatively thin as compared, for example, a cathode ray tube (CRT) or the like.

As would be appreciated by those of ordinary skill in the art, display screen 64 is operatively coupled to the computer circuitry disposed within housing 60 and is adapted to provide a visual display of graphics and/or data under control of the internal computer.

Programmer 20 described herein with reference to FIG. 2 is described in more detail in U.S. Pat. No. 5,345,362 issued to Thomas J. Winkler, entitled Portable Computer Apparatus With Articulating Display Panel, which patent is hereby incorporated herein by reference in its entirety. The Medtronic Model 9790 programmer is the implantable device-programming unit with which the present invention may be advantageously practiced.

Figure 4:
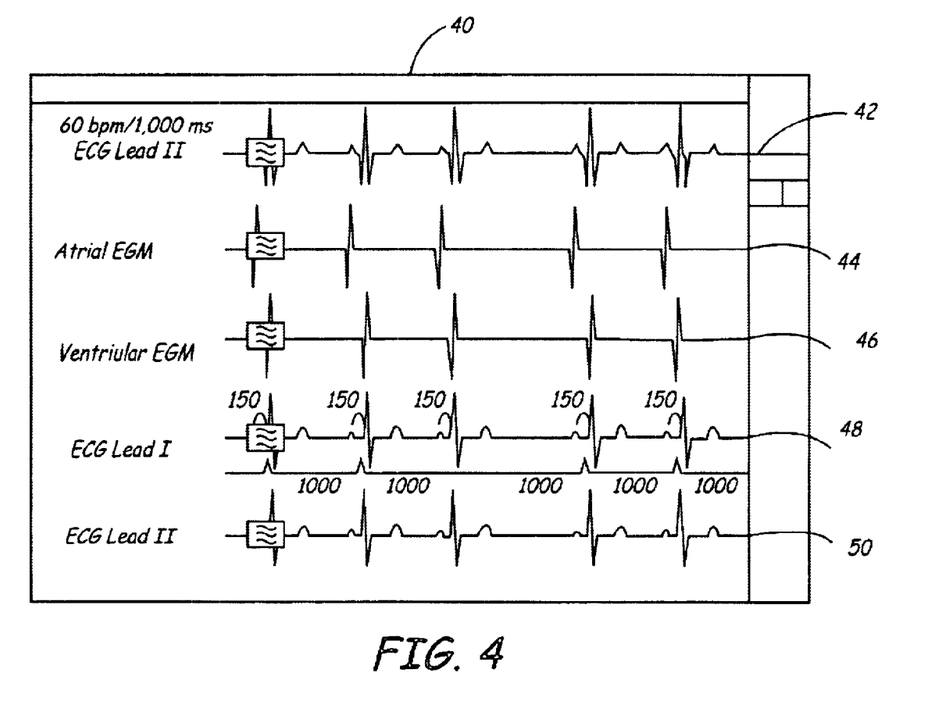
FIG. 4 is a pictorial representation of a typical display screen showing a plurality of continuous, real-time waveforms.

FIG. 4 shows various signals 42, 44, 46, 48, and 50 that are continuously scrolling across the display screen 40 of programmer 20 (FIG. 3). EGM tracings 44 and 46 are taken from electropotentials sensed by the implanted lead system. ECG tracings 42, 48, and 50, however, are of particular note regarding the presently disclosed invention.

Typically, two or three of the skin-mounted electrodes will be mounted on the patient's body in such a way that all three ECG vectors 42, 48, or 50 will be displayed on screen 40. One of the three may be selected for display as the tracing that will appear on other screens, e.g., programming screen. The electrodes are positioned on the patient's body in a manner of practice known in the art. It is expected that skin-mounted electrodes of the present invention will provide high quality ECG readings sufficient for use in diagnosis and therapy.

Figure 5:
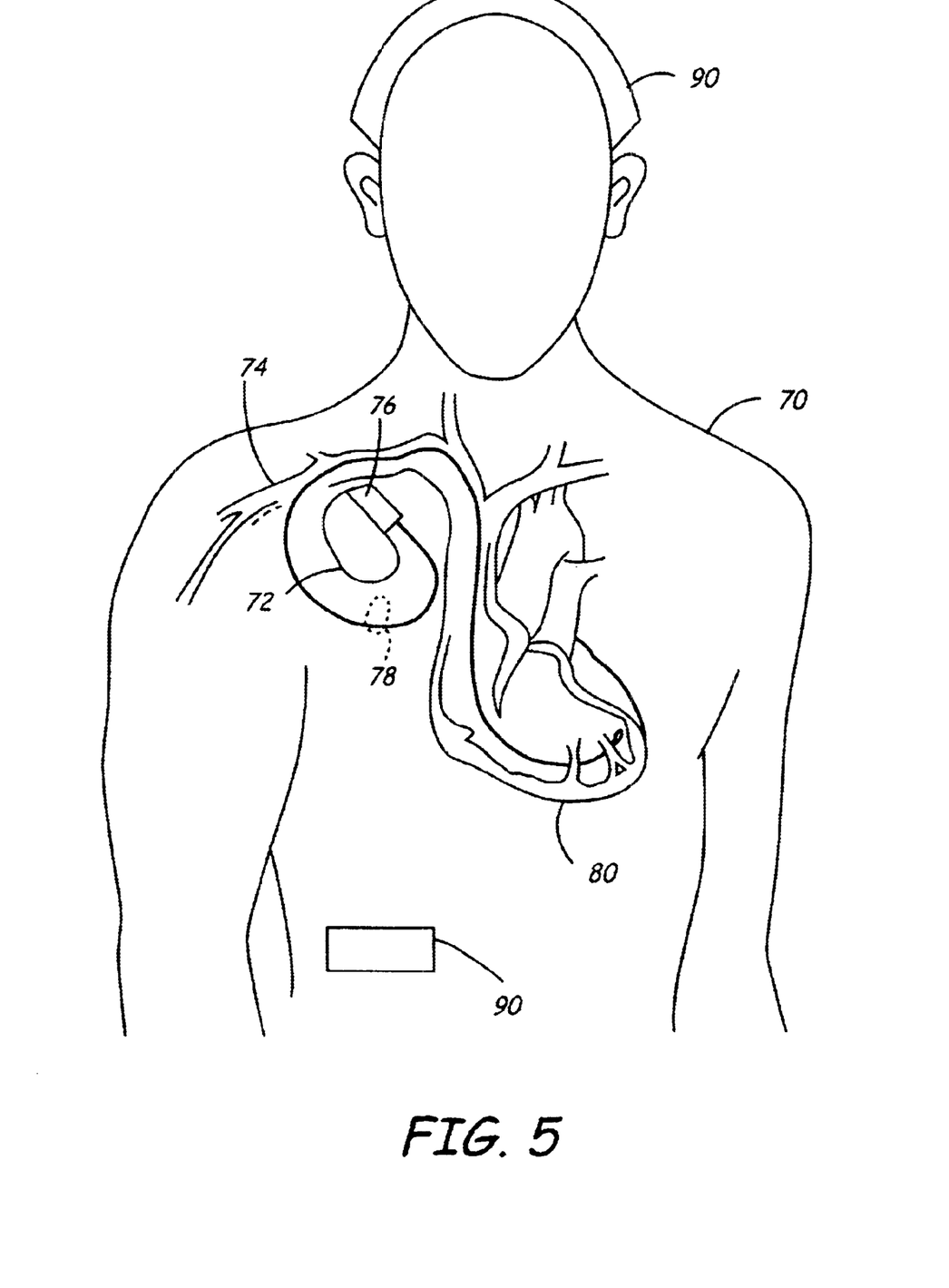
FIG. 5 is an illustration of an implantable medical device system with a skin-mounted memory patch placed on the patient's body in accordance with the second embodiment of the present invention.

FIG. 5 is an illustration of an implantable medical device system adapted for use in accordance with one embodiment of the present invention. The medical device system shown in FIG. 1 includes an implantable device 72, such as a pacemaker or defibrillator, among others, which has been implanted in patient 70. In accordance with conventional practice in the art, pacemaker 72 is housed within a hermetically sealed, biologically inert outer casing, which may itself be conductive so as to serve as an indifferent electrode in the pacemaker's pacing/sensing circuit. One or more pacemaker leads, collectively identified with reference numeral 78 in FIG. 5 are electrically coupled to pacemaker 72 in a conventional manner at 76 and extend into the patient's heart 80 via a vein 74. Disposed generally near the distal end of leads are one or more exposed conductive electrodes for receiving electrical cardiac signals and/or for delivering electrical pacing stimuli to heart 80. As will be appreciated by those of ordinary skill in the art, leads 78 may be implanted with its distal end situated in the atrium and/or ventricle of heart 80. Disposed externally on the body of patient 70 is memory patch 90. Memory patch 90 may be taped either over the device in accordance, for example, with near-field telemetry such as described in U.S. Pat. No. 4,556,063 incorporated herein by reference in its entirety. Patch 90 may also be mounted on the head in the form of a helmet, skull cap or similar structure to collect EEG signals at the scalp. Alternatively, patch 90 may be taped anywhere on the body for use in systems that implement telemetry-based data collection from implanted devices as described in body wave/bus telemetry in the above referenced Ryan '636, Funke '897 and '859 patents or far field telemetry as described in U.S. Pat. Nos. 5,683,432 and 5,843,139 issued to Goedeke, all incorporated herein by reference in their entirety. As the memory of implanted device 72 fills up, the data is transmitted to memory patch 90 for storage, thus making memory space available in device 72.

Implantable medical device 72 may be one or a combination of pacemaker/cardioverter/defibrillator (PCD). Peripheral memory patch 90 of the present invention may be practiced in conjunction with PCDs, such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless, or U.S. Pat. No. 4,821,723 to Baker et al., all hereby incorporated herein by reference in their respective entireties.

Alternatively, medical device 72 may be an implantable nerve stimulator or muscle stimulator, such as those disclosed in U.S. Pat. No. 5,199,428 to Obel et al., U.S. Pat. No. 5,207,218 to Carpentier et al., or U.S. Pat. No. 5,330,507 to Schwartz, or an implantable monitoring device, such as the Medtronic chronicle as substantially described in U.S. Pat. No. 5,331,966 issued to Bennett et al., all of which are hereby incorporated herein by reference in their respective entireties. The implantable monitoring device may monitor any or a combination of the following parameters: oxygen, pressure, cardiac flow, stroke volume, cardiac acceleration, and the like.

Accordingly, the present invention is believed to find wide application with any implantable device which requires storage of appreciable amounts of physiologic, diagnostic, system, or other medical data, particularly those that acquire such information on a continuous or near continuous basis.

In general, implantable medical device 72 shown in FIG. 1 includes a hermetically-sealed enclosure that may include various elements, such as an electrochemical cell, circuitry that controls device operations and records arrhythmic EGM episodes, telemetry transceiver antenna and circuit that receive commands from and transmit stored data to an external programmer via telemetry. The telemetry transceiver antenna and circuit may further transmit stored data in a telemetry uplink to a peripheral memory patch of the present invention.

Figure 6:
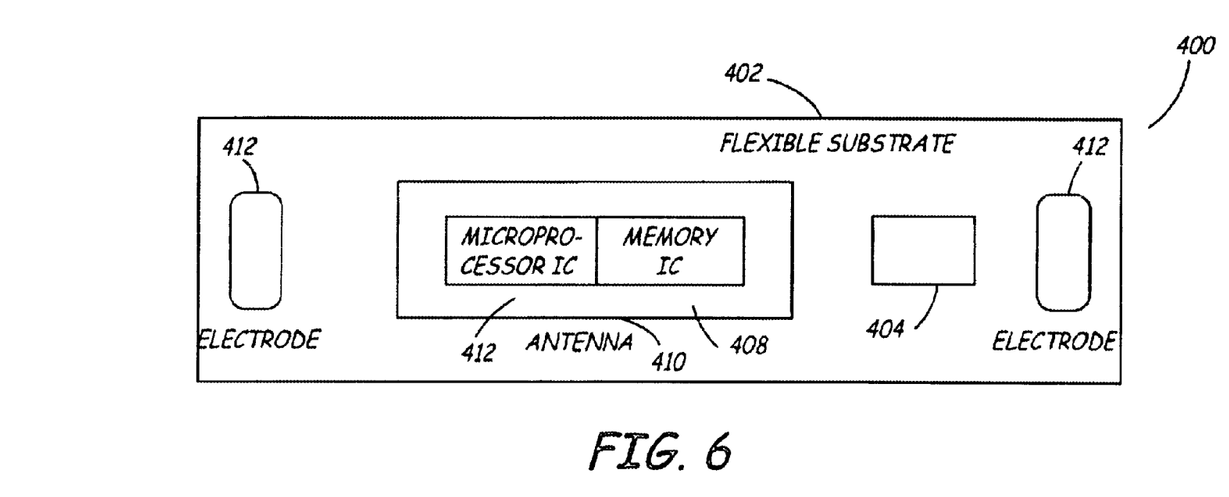
FIGS. 6 and 7 respectively show top and side cross-sectional views of a peripheral memory module in accordance with the second embodiment of the present invention.
Figure 7:
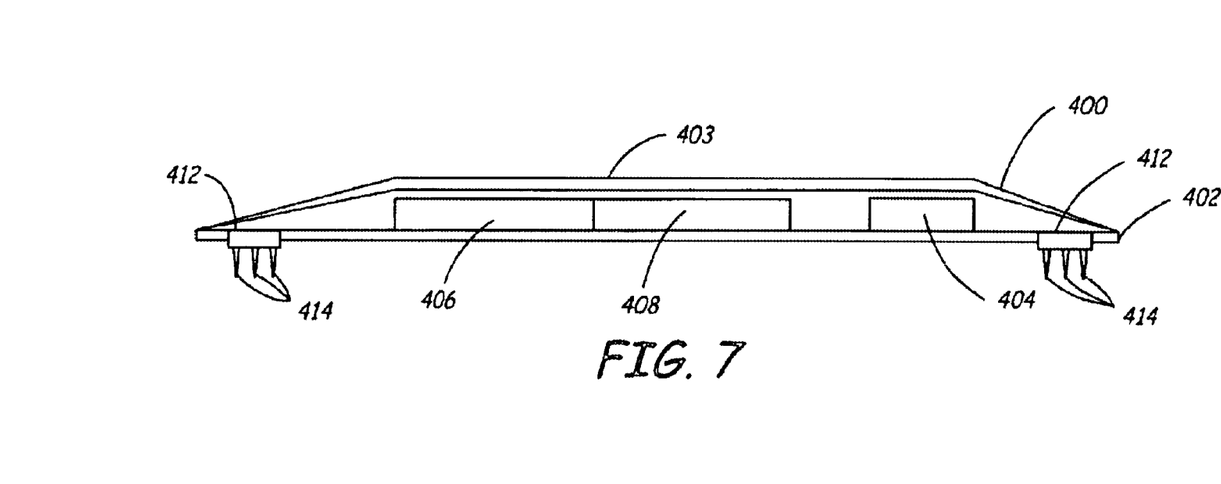

FIGS. 6 and 7 respectively show top and side cross-sectional views of a peripheral memory module in accordance with one embodiment of the present invention. Peripheral memory patch 400, in accordance with the embodiment depicted in FIGS. 6 and 7, is provided on a flexible substrate 402. Substrate 402 includes an adhesive backing (not shown) that provides for both comfort and extended periods of wear when affixed directly on the patient's skin. Attached to the electrodes are a plurality of nano spikes 414 that penetrate the cornified layer of a dermal tissue and hold the memory module in place. Even more importantly, nano spikes 414 position electrodes 412 so they make intimate contact with the epidermis. With good electrical contact, the electrodes can receive telemetered data from an implantable device, as is described in the previously referenced '265 patent.

It is contemplated that peripheral memory patch 400 may be attached to a patient's skin for periods of about one to two days. Under certain conditions extended periods of wear on the order of one to two weeks may be desirable.

In the embodiment illustrated in FIGS. 6 and 7, flexible substrate 402 may comprise a resilient material upon which several electronic and electrical components are mounted. Flexible substrate 402 may include an integral or separate interconnect pattern of electrical conductors that provide for interconnection between the various components disposed on flexible substrate 402. Suitable materials that may be used to fabricate flexible substrate 402 include, without limitation, mylar, flexible foil, flex PC, Kapton, polymer thick film (PTF) or equivalent.

The electronic portion of peripheral memory patch 400 includes a microprocessor integrated circuit (IC) 406 and a memory IC 408. Shown surrounding microprocessor 406 and memory 408 is an antenna 410 which receives uplinked physiologic data transmitted by an implantable medical device or another data source in data communications with memory patch 400. Also provided on flexible substrate 402 is a battery 404 and one or more electrodes 412. In this embodiment, flexible substrate 402 and the various components populating flexible substrate 402, which make up the electronics module of peripheral memory patch 400, are fabricated and packaged in accordance with various known "smart card" technologies, examples of which are disclosed in U.S. Pat. Nos. 5,311,396 and 5,480,842, both of which are incorporated herein by reference in their respective entireties.

The electronics module of peripheral memory patch 400 may include a flexible foil substrate 402 with an attached battery 404 and chip-on-board (COB) memory chips 408. In accordance with one embodiment, battery 404 may have a lithium manganese oxide, $LiMnO_2$, chemistry, and may be of a sealed foil design. Although a rectangular shape is shown in FIGS. 6 and 7, various other component geometries, such as square, round or oval shapes, may be used.

Memory 408 may constitute a single memory IC or several memory ICs. Memory 408 is preferably a state-of-the-art, commercially-available memory which may be embodied in various memory technologies (e.g., CMOS). Memory 408, for example, may include one or more dynamic random access memories (DRAMs), static random access memories (SRAMs), electrically erasable programmable read-only memories (EEPROMs), flash memories, ferroelectric memories, and/or analog memories.

Memory 408 of peripheral memory patch 400 may be configured using 128 megabyte (MB) DRAMs or 128 MB flash memories in contrast to a 32 kilobyte (KB) times 8 SRAMs or 256 KB times 8 SRAMs which are suitable for use as internal memories 220 of implantable medical devices 216.

Further examples of suitable DRAMs that are commercially-available and may be employed in peripheral memory patch 400 include models MT48LC2M8A1 (16 MB), MT48LC8MA82 (64 MB), and MT48LC16M8A2 (128 MB), all of which are manufactured by Micron Corporation. An example of a suitable analog memory which may be employed in peripheral memory patch 400 is described in U.S. Pat. No. 5,312,446, which is incorporated herein by reference in its entirety.

Figure 8:
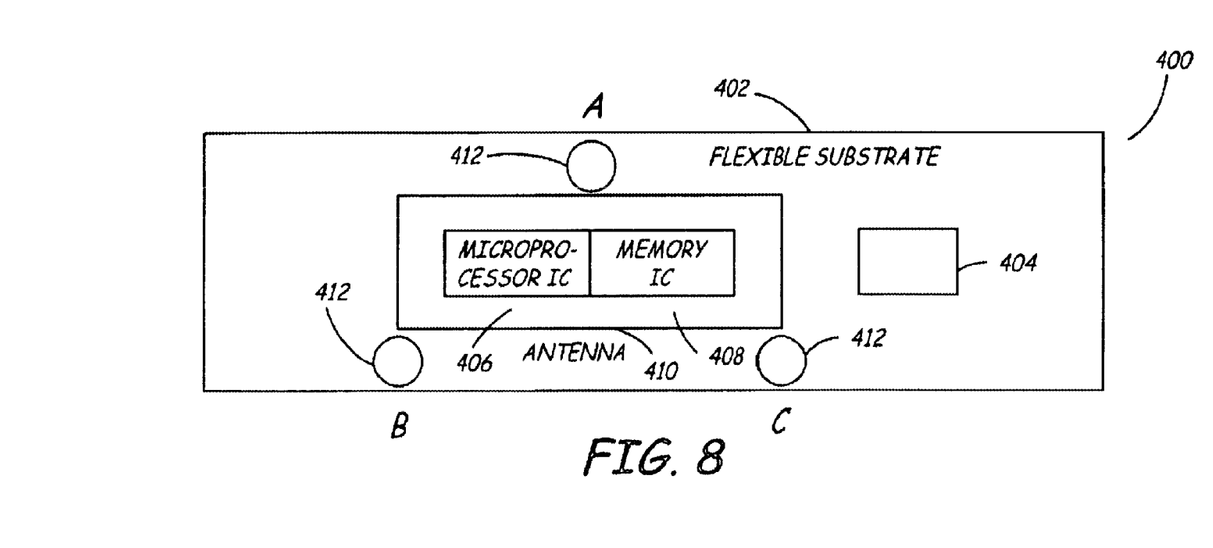
FIGS. 8 and 9 respectively show top and side cross-sectional views of a peripheral memory module in accordance with the third embodiment of the present invention.
Figure 9:
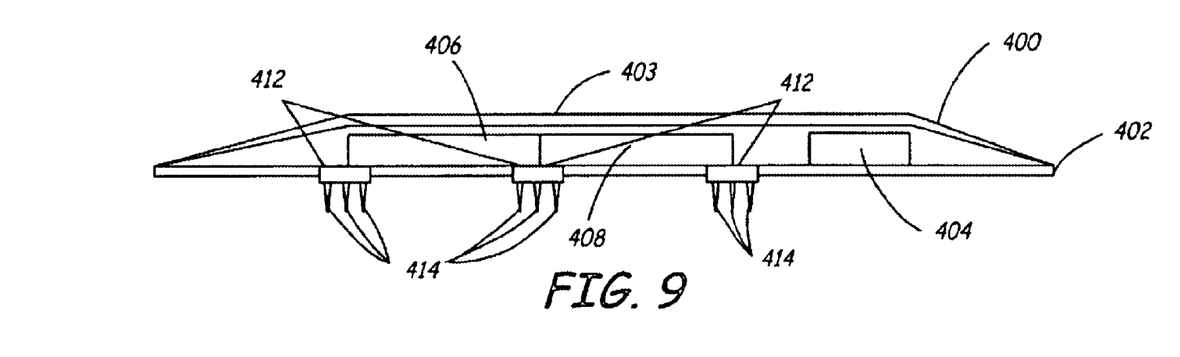

FIGS. 8 and 9 respectively show top and side cross-sectional views of a peripheral memory module in accordance with another embodiment of the present invention. In this embodiment, electrodes 412 are used to detect cardiac depolarizations directly, rather than serving as receptors of digital information as disclosed in other embodiments. Further, the device illustrated in FIGS. 8 and 9 may be attached to the patient's body for extended periods of time, e.g. for up to 7 days.

The present invention, in accordance with FIGS. 8 and 9, may be used to replace an insertable loop recorder, a minimally invasive device to monitor physiologic events manufactured by Medtronic, Inc. and described in the above referenced '352 patent, issued to Klein, et al and incorporated herein by reference in its entirety. The device described in the '352 provides long-term ECG monitoring, with the capability for using manual or automatic triggers or both, to cause the memory to store events in reserved areas of a looping memory, preferably in identifiable memory partitions. This minimally implantable device is designed to accept limited programming or mode control and can read out sections of some or all of the memory when prompted from the outside by the physician or other user, provided they use the appropriate external programmer to initiate and receive such transmissions from the implanted device or other data source.

Similarly, the present invention, as disclosed in FIGS. 8 and 9, may have a looping memory residing in memory IC 408 that, under the control of microprocessor IC 406 will be activated to record and retain an ECG record of a detected cardiac arrhythmia, as substantially described in the above referenced '966 patent. When implemented in this manner, however, electrodes 412 serve as ECG electrodes. Also, in this embodiment, ECG electrodes are positioned in an orthogonal configuration so that the device may detect cardiac depolarizations optimally. It is well known in the art that an orthogonal configuration for ECG electrodes 412 lends itself to optimal sensing of cardiac depolarization, especially when the electronic device is able, as this one is, to switch automatically to any vector (AB, AC, or BC) that provides the best view of the desired cardiac depolarization. This orthogonal configuration of electrodes is disclosed in pending application Ser. No. 09/797,031, Implantable Medical Device With Multi-Vector Sensing Electrodes, filed Mar. 1, 2001 and assigned to the assignee of record, Medtronic, Inc.

The present invention relates to multi vector sensing of cardiac depolarizations that form the basis of an ECG tracing, as opposed to, for example, the single vector sensing disclosed in the '352 patent. The proposed orthogonal electrode configuration used in the present invention, with an improved algorithm as compared to that proposed in the '966 patent, provides a more flexible and optimal system for sensing cardiac depolarizations. In addition, the present invention includes novel shapes that are structured to promote stability of the ILR, post implant, within the incision pocket under the skin. The increased number of electrodes, typically three, makes the ILR less susceptible to electrical interference and motion artifacts as well as less sensitive to the need for specific and exclusive device orientations and implants sites.

This invention also includes specific algorithms that stand in sharp contrast with the '966 patent. Specifically, the invention provides user-programmable software that offers the user the ability to select the best vector to detect the greatest amplitude signal for the PQRST complex, thereby enhancing the sensing of cardiac depolarizations. At the same time, however, the user may also use the software to program a non-orthogonal vector setting, if that proves satisfactory for sensing cardiac depolarizations.

Further referring to FIGS. 8 and 9, the present invention includes numerous novel features that provide significant advancements in the art. The multi-vector electrode configuration provides, inter alia: the ability to record multi-vector ECG tracings; the choice of using the one vector that provides optimal signal quality; orthogonal electrode configurations that are well known for their optimal and flexible sensing; and the availability of these features without the need for an implanted device.

The benefits to the patient are many. There is convenience to the patient because the skin need not be pre-modified, pre-conditioned or prepared to accept the nano spikes. There is less time involved in placing such electrodes. Further, applying an ECG electrode is less intrusive for a patient, in that the nurse/technician merely places the adhesive-equipped electrode under clothing on skin easily reached by the fingers. There is less patient pain and discomfort, since the needles/knives/spikes are structured to avoid deep skin penetration that may result in nerve and capillary aggravation or damage.

The present invention promotes better contact with conductive tissue particularly in systems that use extended memory to collect chronic or long-term physiological data. Further, in implementations incorporating telemetry data transmission systems, better signal capture and operational efficiencies are achieved.

The preceding specific embodiments are illustrative of the practice of the invention. It is to be understood, therefore, that other expedients known to those of skill in the art or disclosed herein may be employed without departing from the invention or the scope of the appended claim. It is therefore to be understood that the invention may be practiced otherwise than is specifically described, without departing from the scope of the present invention. As to every element, it may be replaced by any one of infinite equivalent alternatives, only some of which are disclosed in the specification.

What is claimed is:

1. A device of wherein for establishing reliable contact with conductive tissue, the device comprising:
    a plurality of shaped nano spikes attachable to the conductive tissue, said plurality of nano spikes including angularly disposed end shapes configured to penetrate the cornified layer of the skin and to contact the conductive tissue at various angles;
    a conductive substrate on said plurality of nano spikes integrated therewith; and
    at least one electrode formed on said substrate to collect biopotential signals sensed by said nano spikes in contact with the conductive tissue.

2. A The device of claim 1 wherein said shapes are formed at protruding extremities of said nano spikes.

3. The device of claim 2 wherein said shapes are selected from one and a combination of pins, knives, spikes, prismatics forming pointed extremities to penetrate the cornified layer of the skin.

4. The device of claim 1 wherein said nano spikes are less than about 10 micron length.

5. A biopotential sensing system in comprising:
    a programmer including computer circuitry and a display screen operatively coupled to said computer circuitry;
    a plurality of nano spikes integrated with at least one skin-mounted electrode substrate to provide said biopotential sensing; and
    an interface providing operable data communication between said at least one skin-mounted electrode substrate and the programmer computer circuitry.

6. The system of claim 5 wherein the at least one skin-mounted electrode substrate provides ECG (electrocardiogram) input to the programmer via the interface.

7. A smart patch attachable to the skin, the smart patch comprising:
    an electrode including a plurality of nano spikes to detect biopotential signals, said nano spikes including angularly disposed end shapes configured to penetrate the cornified layer of the skin and to contact conductive tissue;
    a microprocessor controller including a programmable memory to store said biopotential signals; and
    a telemetry transceiver to operate in a bi-directional data communication mode under the control of the microprocessor.

8. The smart patch of claim 7 wherein said telemetry transceiver transmits said biopotential signals to another device.

9. The smart patch of claim 7 wherein said electrodes include electrodes positioned in orthogonal configuration.

10. The smart patch of claim 7 wherein the smart patch is implemented to replace an ILR (implantable loop recorder) device.

11. The smart patch of claim 9 wherein the smart patch is implemented to replace difficult to apply electrodes for EEG (electroencephalogram) input.

12. The smart patch of claim 7 wherein the biopotential signals comprise electroencephalograms.

13. The smart patch of claim 7 wherein said patch is implemented to collect data from a body bus medical device.

14. The smart patch of claim 7 wherein said patch is detachable and adaptable for downloading data stored in the programmable memory.

15. The smart patch of claim 7 wherein drug and agent delivery from a device is controlled by the biopotential signals sensed at the electrodes.

16. The smart patch of claim 7 wherein said telemetry is implemented to collect data from various devices.

17. The smart patch of claim 16 wherein said various devices consist of the group selected from pacemakers, defibrillators, Chronicle™, neurological devices, drug administration devices and a combination thereof.

18. The smart patch of claim 16 wherein said data collected from said various devices is transmitted to another device or data collection center.

* * * * *

UNITED STATES PATENT AND TRADEMARK OFFICE
CERTIFICATE OF CORRECTION

| | |
|---|---|
| PATENT NO. | : 6,690,959 B2 |
| DATED | : February 10, 2004 |
| INVENTOR(S) | : David L. Thompson |

It is certified that error appears in the above-identified patent and that said Letters Patent is hereby corrected as shown below:

Column 12,
Line 11, delete "system in comprising" and insert -- system comprising --.

Signed and Sealed this

Thirtieth Day of May, 2006

JON W. DUDAS
*Director of the United States Patent and Trademark Office*